United States Patent [19]

Rasmussen

[11] 4,229,462

[45] Oct. 21, 1980

[54] METHOD FOR CONTROLLING HYPERTENSION AND COMPOSITIONS

[75] Inventor: Chris R. Rasmussen, Ambler, Pa.

[73] Assignee: McNeilab, Inc., Fort Washington, Pa.

[21] Appl. No.: 972,579

[22] Filed: Dec. 22, 1978

[51] Int. Cl.² ........................................... A61K 31/415
[52] U.S. Cl. ................................................ 424/273 R
[58] Field of Search ......................................... 424/273

[56] References Cited

U.S. PATENT DOCUMENTS

| | | | |
|---|---|---|---|
| 3,168,520 | 2/1965 | Kleemann et al. | 544/332 |
| 4,025,517 | 5/1977 | Rasmussen | 424/273 |
| 4,058,557 | 11/1977 | Douglas et al. | 424/273 |

Primary Examiner—Frederick E. Waddell

[57] ABSTRACT

A method for controlling hypertension by administering to hypertensive subjects a N-aryl-N'-(2-imidazolidinylidene)urea compound and compositions suitable therefor are described.

17 Claims, No Drawings

METHOD FOR CONTROLLING HYPERTENSION AND COMPOSITIONS

FIELD OF INVENTION

This invention relates to method for controlling hypertension employing N-aryl-N'-(2-imidazolidinylidene)urea compositions.

PRIOR ART

Certain imidazolidine ureas are known in the art. Thus, in U.S. Pat. No. 3,168,520 imidazolidine ureas and hexahydropyrimidine ureas are taught. These compounds are taught to be useful as dye stabilizers. The patent specifically teaches 2-phenylcarbiliminoimidazolidine which is N-(2-imidazolidinylidene)-N'-phenylurea. There is no teaching or suggestion in the patent however for the use of imidazolidineureas and hexahydropyrimidineureas as active ingredients in pharmaceutical compositions.

Some urea compounds have been disclosed to have certain pharmacological properties. Thus, U.S. Pat. No. 4,060,635 discloses amidinoureas. These compounds have an aryl group on one urea nitrogen and a substituted amidino group on the other urea nitrogen. U.S. Pat. Nos. 3,539,616 and 3,784,582 teach amidinoureas in which one urea nitrogen is substituted with an aryl group and the other urea nitrogen is substituted with an unsubstituted amidino group. U.S. Pat. No. 4,058,557, also directed to amidinoureas but more remote, teaches compounds in which one of the amidino nitrogens necessarily is attached to an oxygen. None of the patents teach or suggest the substitution of an imidazolidino group on a urea nitrogen. None of these patents teach or suggest anti-hypertensive activity.

A recent publication, G. H. Douglas et al., Arz. Forsch/Drug Res. 28(II), 1480 (1978) discloses the results of many aryl substituted amidinoureas screened for antimotility and antisecretory activity. N-(2,6-Dimethylphenyl)-N'-(2-imidazolidinylidene)urea and N-(2,6-dimethylphenyl)-N'-(1-methyl-2-imidazolidinylidene)urea are among the compounds tested. No other pharmacological test is reported or use suggested for these compounds.

DESCRIPTION OF THE INVENTION

This invention is concerned with a method for treating hypertension by administering to a subject requiring therapy, a composition comprising a N-aryl-N'-(2-imidazolidinylidene)urea compound of the formula

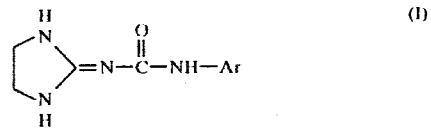

or a pharmaceutically acceptable acid addition salt thereof. It also embraces compositions suitable for such application wherein the foregoing urea compound is in admixture with a pharmaceutically acceptable carrier.

In the foregoing and subsequent formulas, Ar is phenyl substituted with from 0 to 3 substituents independently selected from groups characterized by the presence of halogen or of a carbon-containing group of from 1 to 2 carbon atoms which is optionally attached to the phenyl through a non-basic hetero atom. Representative substituents are halo, such as fluoro, chloro and bromo; lower alkyl such as methyl and ethyl; lower alkoxy, such as methoxy and ethoxy; trifluoromethyl; methylthio; methylsulfonyl; methylsulfinyl; and cyano. In the most preferred compounds, Ar may be represented by

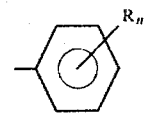

wherein R is methyl, ethyl, chloro, bromo, or methoxy and n is an integer of from 0 to 3.

The activities of the above compounds reside in the urea base so that useful acid addition salts may be from various acids provided only that the acids be pharmaceutically acceptable. Representative acid salts include hydrochloride, hydrobromide, hydroiodide, phosphate, sulfate, p-toluenesulfonate, benzenesulfonate, malate, tartrate, fumarate, citrate, pamoate, maleate, malonate, succinate, oxalate, methosulfate, methanesulfonate, 2-napsylate and the like.

The pharmacologically useful N-aryl-N'-(2-imidazolidinylidene)urea compounds are prepared by substantially two methods. The most generally useful method is by the reaction of an appropriate 2-iminoimidazoline (II) with an aryl isocyante (III) according to the following equation:

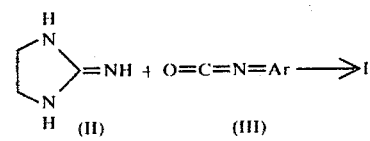

The 2-iminoimidazoline starting materials conveniently may be prepared (according to art methods and as subsequently described) and stored as an acid addition salt

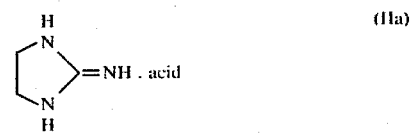

Thus, the initial step is usually the conversion of the acid addition salt to the free base. This may be carried out by thoroughly stirring a solution or suspension in tetrahydrofuran of the acid addition salt with two molar equivalents of 50 percent aqueous sodium hydroxide, followed by the addition of anhydrous sodium sulfate to remove excess water. The thus obtained biphasic mixture is contacted with an appropriate aryl isocyanate to produce the desired N-aryl-N'-imidazolidinylideneurea compound.

In a preferred method for carrying out the reaction between the aryl isocyanate and the 2-imidazolidine, a solution of aryl isocyanate in tetrahydrofuran is added portionwise with stirring to the biphasic mixture at temperatures in the range of about 20° to 30° C. and the mixture stirred for from a few hours to overnight. The N-aryl-N-'-imidazolidinylideneurea compound thus obtained is recovered, converted to an acid addition salt form, if desired, and purified employing conventional procedures.

The free base may be generated by another procedure in which a solution of 2-iminoimidazolidine acid addition salt is brought into contact with a suspension of lithium hydride, preferably, in the same solvent, in an inert atmosphere. Suitable solvents include dry dimethylformamide, dimethylsulfoxide, tetrahydrofuran, and the like. The temperature for addition is generally in the range of 0° to 30° C. An inert atmosphere is conveniently provided by use of nitrogen or argon.

In a preferred method for carrying out the reaction, a solution of 2-iminoimidazolidine acid addition salt is added dropwise with stirring to a cooled suspension of lithium hydride in a dry solvent under nitrogen atmosphere while maintaining temperatures in the 0°–5° C. range. Stirring is continued after the completion of the addition while the mixture is gradually allowed to warm to room temperature to obtain the free base.

The reaction between 2-iminoimidazolidine and aryl isocyanate may be carried out by adding a solution of an aryl isocyanate, dropwise with stirring and cooling, to the reaction mixture containing the free base in an inert atmosphere, stirring the resulting mixture while gradually warming to ambient temperature and thereafter in the temperature range of from about 30° to 110° C., preferably in the range of 65° to 110° C. for optimizing yields, to obtain the desired N-aryl-N'-(2-imidazolidinylidene)urea product. When the reaction is carried out at ambient temperatures, stirring is usually continued for several hours or overnight; when it is carried out at the elevated temperatures, about two hours is satisfactory.

A second general but less preferred method for the preparation of N-aryl-N'-(2-imidazolidinylidene)urea compounds proceeds through the following sequence of reactions.

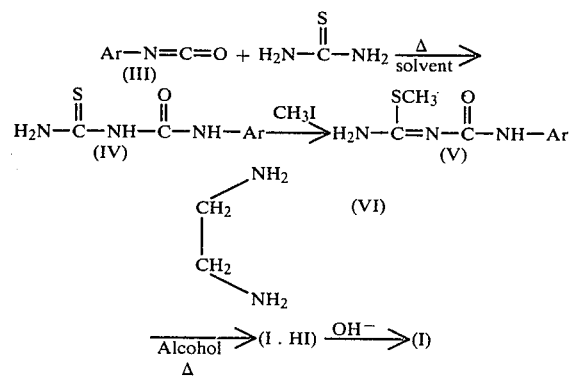

It is seen that the initial step is a reaction between an appropriate aryl isocyanate (III) and thiourea to produce a N-arylthioimidodicarbonicdiamide (IV) which is then reacted with methyl iodide to produce a methyl N'-[(arylamino)carbonyl]carbamimdothioate (V). The latter when reacted with an appropriately substituted ethylenediamine (VI) produces the N-aryl-N'-(2-imidazolidinylidene)urea (I) as a hydroiodide addition salt and which may be converted to the free base by conventional means. The foregoing reaction sequence however is not applicable for the preparation of urea compounds in which the aryl group is a 2,6-disubstituted phenyl group.

The first step may be carried out employing a modification of a procedure reported by Lakra et al., (J. Am. Chem. Soc. 51, 2220 (1929)) in which an appropriate aryl isocyanate (III) and thiourea are reacted to produce a N-arylthioimidodicarbonic diamide compound (IV), hereinafter referred to for convenience as a "thiobiuret compound". For the reaction, substantially equimolar amounts of the reactants, preferably a slight excess of the thiourea, are employed. The temperature for the reaction may be in the range of from about 80° to 120° C. The reaction is preferably carried out in a solvent. Suitable solvents include dimethylformamide, dimethyl sulfoxide, and the like.

The reaction is preferably carried out by heating the isocyanate and thiourea at steam bath temperature for from about two to twelve hours whereupon the thiobiuret compound (IV) is formed in the reaction mixture. The mixture is then diluted with water and cooled to induce crystallization of the thiobiuret compound which is then separated from the reaction mixture and purified employing conventional procedures.

In the second step of the reaction, the N-aryl thiobiuret compound and an S-methylating agent are reacted to produce a methyl N'[(arylamino)carbonyl]carbamimidothioate compound (V), hereinafter referred to for convenience as the "thioate compound". Substantially equimolar amounts of the reactants, preferably a slight excess of methylating agent, are employed. Although other methylating agents such as dimethyl sulfate and the like also may be used, methyl iodide is preferred. A solvent is preferably employed. Suitable solvents include acetone, methanol, ethanol, isopropanol, and the like. The temperature of the reaction may range from ambient to reflux temperatures, ambient temperatures being preferred.

The reaction is conveniently carried out by mixing together the thiobiuret compound and methyl iodide in methanol at ambient temperature for several hours. The product which forms in the reaction mixture as its hydroiodide addition salt is recovered and purified, if desired, employing conventional procedures.

In the third step, the thioate compound (V) as the hydroiodide salt and an appropriate ethylenediamine compound (VI) are reacted to produce the desired N-aryl-N'-imidazolidinylideneurea product as a hydroiodide salt. Substantially equimolar amounts of the reactants are employed. The reaction is preferably carried out in methanol and other lower alkanols, methanol being preferred.

The reaction is conveniently carried out by refluxing together the hydroiodide salt of (V) and the ethylenediamine compound in methanol for from about one to several hours and thereafter vaporizing the solvent to obtain as residue the desired N-aryl-N'-imidazolidinylideneurea product as a hydroiodide salt. The product may then be recovered and purified employing conventional procedures.

The salt may be converted to the free-base. If another salt is desired, the free base is caused to react with another acid to form a desired acid addition salt. Conventional procedures may be employed for these conversions. Thus, for example, a representative convenient procedure for obtaining the free base from the salt is dissolving the acid addition salt in a minimal amount of lower alkanol solvent such as methanol or ethanol, warming with an organic base such as triethylamine and the like, and cooling to obtain the free-base product as a crystalline solid. Similarly, a representative convenient procedure for converting the free base to an acid addition salt is mixing the base with an alcoholic solution of an acid corresponding to the addition salt desired and cooling to obtain the acid addition salt.

The N-aryl-N'-(2-imidazolidinylidene)urea compounds have been found to alleviate hypertension and further, to generally accomplish this without an accompanying increase in heart rate. An agent which has an antihypertensive effect without increasing, but rather maintaining or decreasing heart rate, is the one considered most useful for beneficially treating a hypertensive subject. The extent to which a compound possesses these properties may be determined in the antihypertensive test on rodents and in the hemodynamic evaluation in dog hereinafter described.

Rodent Antihypertensive Screen

This test evaluates compounds for effects on arterial pressure and heart rate. In this test, the arterial pressure of spontaneously hypertensive rats or rats made hypertensive with injections of desoxycorticosterone acetate and 2 percent sodium chloride for drinking water, is monitored directly via an aortic cannula. Rats are anesthetized with an inhalation anesthetic (methoxyflurane or ether). The left carotid artery is isolated and cannulated. The tip of the cannula is advanced to the aorta and the cannula is exteriorized behind the neck at the level of the scapula. Animals are placed in individual cases and allowed to recover from the anesthetic and are kept unrestrained. The arterial cannula is connected to the presssure transducer which is attached to the recorder. Heart rate is determined from the arterial pressure recording. Animals with pressures greater than 149 millimeters of mercury are considered sufficiently hypertensive to be employed in the test for antihypertensive effects. The test compounds are administered either orally (p.o) by gavage or by intraperitoneal (i.p.) injection. The arterial pressure and heart rate are monitored for a minimum of 4 hours. A test compound is considered to be active as an antihypertensive agent if the mean arterial pressure (MAP) indicates a fall of > 19 mm of Hg. Each animal serves as his own control.

The results of this test employing two rats for each compound and performed with N-aryl-N'-(2-imidazolidinylidene)urea compounds are shown in Table I.

Hemodynamic Evaluation in Dog.

This test is used to evaluate the effects of a given compound on both the cardiovascular and autonomic nervous systems in normal anesthetizedanimals.

In this test, mongrel dogs are anesthetized with 20 mg/kg (milligrams per kilogram of body weight) of thiopental sodium and 60 mg/kg of alpha-chlorolose. Supplemental alpha-chlorolose (60 mg/kg) is used for maintenance of anesthesia, if necessary. A cuffed endotracheal tube is inserted to maintain an unobstructed airway, and the animal is respired with a ventilation pump. A femoral artery and vein are catheritized for recording of arterial pressure and for intravenous injections, respectively. Both common carotid arteries are isolated for performance of bilateral carotid occlusion. The vagus nerve is stimulated electrically at the peripheral end for ten seconds with five volts at 20 pulses per second each with a two milli-second duration to obtain cardiac arrest. The electrocardiogram is monitored through Limb Lead II.

Control cardiovascular responses are obtained to the following pharmacological procedures: 1.0 mcg/kg I.V. (microgram per kilogram of body weight, intravenous) of l-epinephrine, carotid occlusion, 10 mcg/kg I.V. of dimethylphenylpiperazinium iodide (DMPP), peripheral vagal stimulation, 10 mcg/kg I.V. of acetylcholine and 2 mcg/kg I.V. of angiotensin. These control responses are produced twice, then the test compound is injected at 5 mg/kg (milligram per kilogram) I.V. employing bolus injections over approximately a one minute period. If no change in arterial pressure, heart rate, or ECG (Limb Lead II) occurs, an additional 5 mg/kg I.V. of the test compound is administered. The effects of the test compound are noted on the electrocardiogram, arterial pressure, and heart rate. Ten minutes after administration of the test compound, another series of hemodynamic responses is obtained.

Employing a dog for each test compound, heart rate data are obtained for N-aryl-N'-(2-imidazolidinylidene)urea compounds. The results from this test are also shown in Table I.

The results seen in Table I shown that N-aryl-N'-(2-imidazolidinylidene)urea compounds and their salts possess not only the beneficial antihypertensive property but also the desirable property of maintaining or lowering normal heart rate. The properties are utilized in the methods and compositions of the present invention.

The process of the present invention, namely, a method for treating hypertension or alleviating high blood pressure, comprises administering to subjects in need of treatment, a therapeutically effective hypertension or arterial pressure reducing amount of a N-aryl-N'(2 imidazolinylidene) urea compound of Formula I or its pharmaceutically acceptable salt as active agent. The active agents may be administered with or without carrier in the amounts hereinafter set forth. A preferred method of administration is by the use of pharmaceutical compositions in unit dosage form as described below.

The operable ranges for carrying out the process is the administration, orally or parenterally, of from about 5 milligrams to about 500 milligrams of a N-aryl-N'-(2-imidazolidinylidene)urea compound in dosage unit form. While the therapeutic method is most useful for human subjects, it may also be employed for other mammals. Operable amounts are generally within the range of from about 0.5 to 50 mg/kg of body weight.

The outstanding properties are most effectively utilized with the pharmaceutical compositions of the present invention. The pharmaceutical compositions comprising a N-aryl-N'(2-imadozolidinylidene)urea compound or acid addition salt thereof, as the active ingredient, may be prepared by intimately mixing the urea compound with a pharmaceutical carrier according to conventional pharmaceutical compounding techniques, which carrier may take a wide variety of forms depending on the form of preparation desired for administration, e.g., oral or parenteral. In preparing the compositions in oral dosage form, any of the usual pharmaceutical media may be employed, including liquid carriers such as water, glycols, oils, alcohols and the like for oral liquid preparations such as suspensions, elixers and solutions; and solid carriers such as starches, sugars, kaolin, calcium stearate, ethyl cellulose, etc., including materials which function as lubricants, binders, disintegrating agents and the like for powders, capsules and tablets. Because of their ease in administration, tablets and capsules represent the most advantageous oral dosage form. These compositions employ solid pharmaceutical carriers such as the aforementioned starches, sugars, kaolin and the like, generally with a lubricant such as calcium stearate. It is especially advantageous to formulate the aforementioned pharmaceutical compositions in dosage unit form for ease of administration and uniformity of dosage. The term "dosage unit form" as used in the specification and claims herein refers to physically discrete units suitable as unitary dosages, each unit containing a predetermined quantity of active ingredient calculated to produce the desired therapeutic effect in association with the required pharmaceutical carrier. Examples of such dosage unit forms are tablets, capsules, pills, powder packets, wafers, teaspoonful, tablespoonful and the like, and segregated multiples thereof. A dosage unit generally will contain from about 5 to about 500 mg of the N-aryl-N'-(2-imidazolidinylidene)urea compound.

EXAMPLE I

N-(2,6-Dichlorophenyl)-N'-(2-imidazolidinylidene)urea Hydrochloride

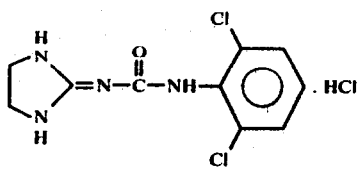

To a stirred suspension of 2.13 grams (0.01 mole) of

TABLE I

ANTIHYPERTENSIVE AND CARDIAC RATE DETERMINATIONS

Compound $$\underset{H}{\overset{H}{N}}\underset{N}{\overset{}{\rangle}}=N-\overset{O}{\underset{\|}{C}}-NH-Ar \cdot HX$$

| Ar | HX | Dose (mg/kg i.p.) | Spontaneously Hypertensive (SH) Rat Maximum Decrease in MAP (mmHg) | Effect on Heart Rate (beats/minute) | Hemodynamic Dog Maximum Decrease in Heart Beat at Dosage 10 mg/kg I.V. (beats/min) |
|---|---|---|---|---|---|
| φ | — | 30 | 72 | +78 | No change (NC) |
| φ | — | 10 p.o. | 39 | −108 | — |
| φ | — | 100 p.o. | 30 | +30 | — |
| 3-Cl φ | HI | 30 | 63 | −42 | −30 |
| 2,6-Cl₂φ | HCl | 20–200 (p.o.) | 39–96 | −39 to −108 | −54 |
| 2,6-(CH₃)₂φ | HCl · ½H₂O | 30 | >19 | ↓* | −60 |
| 2-Cl,6-CH₃φ | HCl | 30 | >19 | ↓ | −42 |
| 2,6-Br₂φ | HCl | 30 | >19 | ↓ | −54 |
| 2-C₂H₅,6-CH₃φ | ½ fumarate | 30 | >19 | ↓ | −42 |
| 4-CH₃φ | HCl | 30 | >19** | NC | NC (5 mg/kg I.V.) |
| 2-OCH₃φ | HCl | 30 | 95 | −108*** | +30*** |
| 2-OCH₃φ | HCl | 10 p.o. | 23 | −84 | — |
| 2-OCH₃φ | HCl | 100 p.o. | 90 | −84 | — |
| 2-Cl φ | HCl | 30 | >19 | −108 | No change |

*Decrease
**One-half the number of rats
***Large slowing effect on spontaneously hypertensive rat regarded to be more meaningful The following examples illustrate the preparation of the N-aryl-N'-(2-imidazolidinylidene)urea compounds and the novel pharmaceutical compositions suitable in the practice of the invention but are not to be construed as limiting:

Starting Material

The 2-imidazolidine starting material of Formula II may be prepared by literature described methods or by the following representative preparation of the hydroiodide addition salt:

213 grams (1.5 moles) of methyl iodide is added with stirring over one hour to a suspension of 153.24 grams (1.5 moles) of ethylenethiourea in 300 milliliters of methanol. Stirring is continued for about an additional hour to complete the formation of S-methyl-ethylene-thiourea. Anhydrous ammonia then is added thereto whereupon a reaction takes place with the formation of 2-iminoimidazolidine hydroiodide and methylmercaptan by-product. The stirring and intermittent addition of ammonia is continued for a total of about 26 hours. The mixture is concentrated with concomitant addition of isopropanol to replace the vaporized methanol, and then cooled and ether added thereto to produce 2-iminoimidazoline hydroiodide as a crystalline solid which after recrystallization from methanol/tert.-butanol has a melting point of 152°–154° C.

Anal. Calcd. for C₃H₇N₃·HI: C, 16.92; H, 3.79. Found: C, 16.85; H, 3.82.

2-iminoimidazolidine hydroiodide in 50 milliliters of dry tetrahydrofuran under an atmosphere of nitrogen is added 0.8 gram (0.01 mole) of aqueous 50 percent sodium hydroxide to produce free 2-iminoimidazolidine base and sodium iodide. Thereafter, 1 gram of anhydrous sodium sulfate is added and the stirring continued for another one-half hour. To the mixture then is added dropwise over a 2.5 hour period, a solution of 0.94 gram (0.005 mole) of 2,6-dichlorophenyl isocyanate in 20 milliliters of tetrahydrofuran and the mixture allowed to stir overnight at room temperature to obtain a N-(2,6-dichlorophenyl)-N'-(2-imidazolidinylidene)urea product. The sodium salts are removed by filtration and the filtrate concentrated on a water bath under reduced pressure to obtain a pale yellow oil. The latter is dissolved in methylene chloride, and the methylene chloride solution first washed with saturated brine, dried over anhydrous potassium carbonate and treated with hydrogen chloride until pH < 3 is reached. The solvent and excess hydrogen chloride are removed in vacuo and the residue recrystallized from methanol/ether to obtain purified N-(2,6-dichlorophenyl)-N'-(2-imidazolidinylidene)urea hydrochloride, m.p. 210°–212° C., which decomposes to a new solid which melts at 239° C.

EXAMPLE II

N-(2-Chloro-6-methylphenyl)-N'-(2-imidazolidinylidene)urea and Hydrochloride

A solution of 10.65 grams (0.05 mole) of 2-iminoimidazolidine hydroiodide in dimethylformamide is added dropwise with stirring over a 15 minute period to a cooled to 5° C. suspension of 397.5 milligrams (0.05 mole) of lithium hydride in 50 milliliters of dry dimethylformamide under nitrogen whereupon hydrogen evolution is observed. While stirring is continued, the mixture is allowed to gradually warm to room temperature. Thereafter, the reaction mixture is cooled to 0°-5° C. and a solution of 5.0 grams (0.03 mole) of 2-chloro-6-methylphenyl isocyanate in 25 milliliters of dry dimethylformamide is added dropwise over a two hour period. After completion of the addition, the mixture is allowed to warm gradually to room temperature while the stirring under nitrogen atmosphere is continued overnight to obtain the desired N-(2-chloro-6-methylphenyl)-N'-(2-imidazolidinylidene)urea product which remains in solution. The product is recovered from the reaction mixture by (a) adding the mixture to 300 milliliters of ice water with stirring, (b) lowering the pH below 2 with aqueous 10 percent hydrochloric acid to precipitate acid insoluble material (c) filtering, (d) basifying the filtrate to pH 8-9 with solid potassium carbonate, and (e) saturating the solution with solid sodium chloride to precipitate the desired N-(2-chloro-6-methylphenyl)-N'-(2-imidazolidinylidene)urea free base as a white solid. The product after washing thoroughly with water has a melting point of 169°-171° C.

The product urea base is dissolved in 30 milliliters of methanol, and methanolic hydrogen chloride added thereto to a pH below 3. Ether is then added whereupon a N-(2-chloro-6-methylphenyl)-N'-(2-imidazolidinylidene)urea hydrochloride product precipitates. The latter is recovered and recrystallized successively from 2-propanol and methanol-ether to obtain a purified product, m.p. 209°-211°, which decomposes to a solid melting at 270° C. (dec.).

Anal. Calcd. for $C_{11}H_{13}ClN_4O.HCl$: C, 45.69; H, 4.88; N, 19.37. Found: C, 45.59; H, 4.93; N, 19.35.

EXAMPLE III

N-(2,6-Dibromophenyl)-N'-(2-imidazolidinylidene)urea Hydrochloride

In a manner similar to that described in Example II, a solution of 12.0 grams (0.0563 mole) of 2-iminoimidazolidine hydroiodide in 50 milliliters of dry dimethylformamide is added dropwise with cooling and under an atmosphere of nitrogen to a suspension of 447 milligrams (0.0563 mole) of lithium hydride in 50 milliliters of dry dimethylformamide. After completion of the addition the mixture is allowed to warm to room temperature over a period of about half an hour, then cooled to 0°-5° C., and a solution of 7.8 grams (0.0282 mole) of 2,6-dibromophenyl isocyanate in 25 milliliters of dry dimethylformamide is added dropwise over a two hour period while maintaining the cooled temperature range. The mixture is then allowed to warm to room temperature and stirred overnight under nitrogen to obtain the desired N-(2,6-dibromophenyl)-N'-(2-imidazolidinylidene)urea product in the reaction mixture. The product is recovered from the reaction mixture by pouring the mixture into 400 milliliters of ice water, acidifying with 10 percent hydrochloric acid to pH below 3, filtering to remove impurities, saturating the filtrate with solid sodium chloride and basifying with potassium carbonate to a pH of 8-9 to precipate the N-(2,6-dibromophenyl)-N'-(2-imidazolidinylidene)urea product as a white solid, m.p. 185°-190° C. (dec.).

The thus obtained base urea product is suspended in 40 milliliters of methanol and methanolic hydrogen chloride added thereto to a pH below 2. Ether is then added to precipitate the N-(2,6-dibromophenyl)-N'-(2-imidazolidinylidene)urea hydrochloride as a white solid, m.p. 200°-202° C. (dec.). After two recrystallizations from methanol/2-propanol/ether, there is obtained a purified product, m.p. 215°-217° C. decomposing to a solid, m.p. 255° C. (dec.).

Anal. Calcd. for $C_{10}H_{10}N_4Br_2O.HCl$: C, 30.14; H, 2.78; N, 14.06. Found: C, 30.12; H, 2.81; N, 14.04.

EXAMPLE IV

In a similar manner the following compound is prepared:

N-(2-Imidazolidinylidene)-N'-(2-methoxyphenyl)urea.hydrochloride, m.p. 197°-199.5° C., by reacting 2-iminoimidazolidine (prepared from 2-iminoimidazolidine hydroiodide and lithium hydride) and 2-methoxyphenyl isocyanate at about 5° to 10° C. to obtain a N-(2-imidazolidinylidene)-N'-(2-methoxyphenyl)urea product, followed by reacting the urea base with methanolic hydrogen chloride and recrystallizing first from methanol/2-propanol, then twice from methanol ether.

Anal. Calcd. for $C_{11}H_{14}N_4O_2.HCl$: C, 48.80; H, 5.58; N, 20.70. Found: C, 48.75; H, 5.61; N, 20.71.

EXAMPLE V

N-(2-Ethyl-6-methylphenyl)-N'-(2-imidazolidinylidene)urea. Fumarate (3:2)

In a manner similar to that previously described, 15.55 grams (0.073 mole) of 2-iminoimidazoline hydroiodide is added dropwise to a dry cooled suspension of 596 milligrams (0.075 mole) of lithium hydride in 30 milliliters of dimethylformamide under an atmosphere of nitrogen. After completion of the addition, the mixture is allowed to warm to room temperature to complete the reaction. Thereafter the mixture is again cooled, a solution of 8.1 grams (0.05 mole) of 2-ethyl-6-methylphenyl isocyanate in 25 milliliters of dry dimethylformamide is added dropwise over a two hour period and then after the resulting mixture is stirred overnight while the temperature is allowed to rise to ambient temperatures to obtain a N-(2-ethyl-6-methylphenyl)-N'-(2-imidazolidinylidene)urea product. The base product is recovered by procedures similar to that previously described and after recrystallization from methanol-water, a purified base product, m.p. 185°-187° C. is obtained.

A solution of 4.32 grams (0.0175 mole) of the base product thus obtained in 35 milliliters of hot isopropanol is mixed with a solution of 2.04 grams (0.0175 mole) of fumaric acid in 35 milliliters of hot isopropanol and the resulting solution is allowed to cool whereupon a N-(2-ethyl-6-methylphenyl)-N'-(2-imidazolidinylidene)urea fumarate addition salt product crystallizes. The salt product after washing first with isopropanol and thereafter with ether melts at 180° C. (dec.). Successive recrystallizations from methanol isopropanol, methanol/ether, and methanol does not produce a salt of reproducibly sharp melting point. Elemental analysis indicates the salt to be formed from three moles of base and two moles of fumaric acid.

Anal. Calcd. for (C$_{13}$H$_{18}$N$_4$O)$_3$.(C$_4$H$_4$O$_4$)$_2$: C, 58.13; H, 6.44; N, 17.31. Found: C, 58.03; H, 6.57; N, 17.59.

EXAMPLE VI

In a similar operation there is prepared N-(2-Chlorophenyl)-N'-(2-imidazolidinylidene(urea.hydrochloride, m.p.187°–189° C. by reacting 2-iminoimidazoline (prepared from 2-iminoimidazoline hydroiodide and lithium hydride in dimethylformamide at about 20° C.) and 2-chlorophenyl isocyanate at about 20°–30° C. overnight, then heating for 15 minutes to 100° C. on a steam bath to obtain a N-(2-chlorophenyl)-N'-(2-imidazolidinylidene(urea product as a crystalline solid, and thereafter reacting the urea base with methanolic hydrogen chloride.

Anal. Calcd. for C$_{10}$H$_{11}$N$_4$OCl.HCl: C, 43.66; H, 4.40; N, 20.36. Found: C, 43.69; H, 4.43; N, 20.36.

EXAMPLE VII

In operations carried out in a manner similar to that described in Examples II–VI, the following compounds may be prepared:

N2-Imidazolidinylidene-N'-(4-methoxyphenyl)urea and its hydrobromide.

N-(2-Chloro-5-trifluoromethylphenyl)-N'-(2-imidazolidinylidene)urea and its tartrate.

N-(4-Fluoro-2,6-dimethylphenyl)-N'-(2-imidazolidinylidene)urea and its malonate.

N-(2-Imidazolidinylidene)-N'-(4-methylphenyl)urea and its hydrochloride, m.p.210°–212° C.

N-(2,4-Dichlorophenyl)-N'-(2-imidazolidinylidene)urea and its hydrochloride, m.p. 217°–219° C.

N-(2,3-Dichlorophenyl)-N'-(2-imidazolidinylidene)urea and its hydrochloride, m.p. 218°–220° C.

N-(3,5-Dichlorophenyl)-N'-(2-imidazolidinylidene)urea and its hydrochloride, m.p. 200°–202° C.

N-(3,4-Dichlorophenyl)-N'-(2-imidazolidinylidene)urea and its hydrochloride, m.p. 217°–219° C.

N-(2,5-Dichlorophenyl)-N'-(2-imidazolidinylidene)urea and its hydrochloride, m.p. 213°–215° C.

N-(2-Imidazolidinylidene)-N'-(2,4,6-trichlorophenyl)urea and its hydrochloride, m.p. 232° C. decomposes to solid, m.p. 260° C. (dec.).

N-(2-Fluoro-6-methylphenyl)-N'-(2-imidazolidinylidene)urea and its hydrochloride.

N-(2-Imidazolidinylidene)-N'-(2-methyl-6-trifluoromethylphenyl)urea and its hydrochloride.

N-(2-Imidazolidinylidene)-N'-(2-methyl-6-methylsulfonylphenyl)urea and its hydrochloride.

N-(2-Cyano-6-methylphenyl)-N'-(2-imidazolidinylidene)urea and its hydrochloride.

EXAMPLE VIII

N-(2-imidazolidinylidene)-N'-phenyl urea and its Hydroiodide

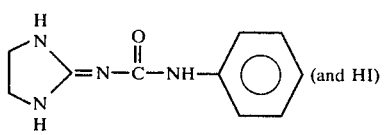
(and HI)

As the first step in the reaction, phenyl isocyanate, 119 grams (1 mole) is added in one portion with swirling to a warm solution of 83.73 grams (1.1 mole) of thiourea in 120 milliliters of dry dimethylformamide and the resulting solution heated for three hours. Thereafter, the solution is cooled, a mixture of ice and ice water cautiously added and the vessel scratched to induce crystallization of the desired intermediate N-phenylthioimidodicarbonic diamide. After crystallization starts, additional ice water (to about 1 liter) is added. The crystals which form are then recovered, washed with water and recrystallized from methanol to obtain 127 grams of a N-phenylthioimidodicarbonic diamide intermediate product, m.p. 176°–180° C.

As a second step, 45.5 grams (0.32 mole) of methyl iodide is added to a solution of 59.5 grams (0.305 mole) of N-phenylthioimidodicarbonic diamide in 300 milliliters of acetone and stirring the resulting mixture for about two hours at room temperature. As a result of these operations crystals form in the reaction mixture which then are filtered and dried to obtain a methyl N'-[(phenylamino)carbonyl]carbamimidothioate hydroiodide product, m.p. 195°–200° C. An analytical sample, m.p. (190°) 200°–202° C. (Hoover) is obtained by recrystallization from methanol.

Anal. Calcd. for C$_4$H$_{11}$N$_3$OS.HI: C, 32.06; H, 3.59; N, 12.46. Found: C, 32.11; H, 3.62; N, 12.48.

Next, a methanol solution of 33.72 grams (0.1 mole) of the thus prepared methyl N'-[(phenylamino)carbonyl]carbamimidothioate hydroiodide and a methanol solution of 6.01 grams (0.1 mole) of ethylenediamine (about 50 milliliters total of methanol) are mixed together and heated under reflux for about 1.5 hours. The mixture is then cooled to −20° C. to crystallize N-(2-imidazolidinylidene)-N'-phenylurea product as its hydroiodide. Several crops are recovered, combined and the combined crops purified by dissolving in methanol, filtering, and evaporating the filtrate to isolate the hydroiodide product as residue.

The hydroiodide product residue is converted to the urea base product and purified by a series of steps including dissolving the residue in a minimal amount of methanol, mixing and warming with 8.0 grams (0.079 mole) of triethylamine, replacing the methanol with ethanol, and then cooling to obtain crystals of N-(2-imidazolidinylidene)-N'-phenylurea base m.p. (181°) 182°–183° C. after recrystallization from methanol.

Anal. Calcd. for C$_{10}$H$_{12}$N$_4$O: C, 58.81; H, 5.92; N, 27.43. Found: C, 58.79; H, 5.92; N, 27.48.

The hydroiodide addition salt after recrystallization from acetone had a melting point of 223°–225° C. (dec.). when immersed at 225° C., m.p. 230° C. (dec.).

Anal. Calcd. for C$_{10}$H$_{12}$N$_4$O.HI: C, 36.16; G, 3.94; N, 16.87; I, 38.21. Found: C, 36.22; H, 3.96; N, 16.88; I, 38.21.

EXAMPLE IX

N-(3-Chlorophenyl)-N'-(2-imidazolidinylidene)urea

In operations carried out in a manner similar to that described in Example VIII, 153.57 grams (1.0 mole) of m-chlorophenyl isocyanate is added to a warm solution of 95.15 grams (1.25 mole) of thiourea in 100 milliliters of dimethylformamide and the resultant mixture warmed overnight on the steam bath to obtain a N-(3-chlorophenyl)thioimidodicarbonicdiamide intermediate product in the reaction mixture. The mixture is then cooled to completely precipitate the desired intermediate product which after recovery by filtration and washing with ether has a melting point of 187°–189° C. (dec.). Additional crops are obtained, combined and recrystallized twice from methanol-water and twice from acetonitrile to obtain a purified product, m.p. 205°–207° C. (dec.)

To a clear solution of 80.3 grams (0.35 mole) of N-(3-chlorophenyl)thioimidodicarbonic diamide (prepared as above-described) is added 75.0 grams (0.525 mole) of methyl iodide and the reaction mixture stirred overnight to obtain the desired methyl N'-{[(3-chlorophenyl)amino]carbonyl}-carbamimidothioate hydroiodide product as a crystalline solid, m.p. 182°–183° C. (dec.).

To 37.1 grams (0.1 mole) of methyl N'-{[(3-chlorophenyl)amino]carbonyl}-carbamimidothioate hydroiodide thus prepared is added 6.0 grams (0.1 mole) of ethylenediamine in 100 milliliters of methanol and the resulting mixture allowed to heat under reflux for five hours. The resulting reaction mixture is evaporated to dryness in vacuo and diluted with tertiary-butyl alcohol to obtain crystals of N-(3-chlorophenyl)-N'-(2-imidazolidinylidene) urea hydroiodide product as a crystalline solid. The crystals are recrystallized from tertiary butyl alcohol several times to obtain a purified product, m.p. 192°–194° C. (dec.).

Anal. Calcd. for $C_{10}H_{11}ClN_4O.HI$: C, 32.76, H, 3.29. Found: C, 32.82, H, 3.33.

The following examples illustrate the novel pharmaceutical compositions but are not to be construed as limiting:

EXAMPLE X 1,000 hard gelatin capsules, each containing 200 milligrams of N-(2,6-dichlorophenyl)-N'-(2-imidazolidinylidene)urea are prepared from the following formulation:

|  | Grams |
| --- | --- |
| N-(2,6-Dichlorophenyl) N'-(2-imidazolidinylidene) urea | 200 |
| Starch | 250 |
| Lactose | 750 |
| Talc | 250 |
| Calcium stearate | 10 |

A uniform mixture of the ingredients is prepared by blending and employed to fill two-piece hard gelatin capsules. The capsules are suitable to be orally administered to hypertensive subjects to reduce blood pressure.

EXAMPLE XI

Gelatin capsules are prepared as described in Example X except that in the formulation, 325 grams of N-(2,6-dimethylphenyl)-N'-(2-imidazolidinylidene) urea is employed as active agent providing capsules containing 325 milligrams of N-(2,6-dimethylphenyl)-N'-(2-imidazolidinylidene) urea.

EXAMPLE XII 1,000 compressed tablets, each containing 500 milligrams of N-(2-imidazolidinylidene)-N'-(2-methoxyphenyl) urea are prepared from the following formulation.

|  | Grams |
| --- | --- |
| N-(2-imidazolidinylidene)- N'-(2-methoxyphenyl)urea | 500 |
| Starch | 750 |
| Dibasic calcium phosphate hydrous | 5,000 |

| | Grams |
| --- | --- |
| Calcium stearate | 2.5 |

The finely powdered ingredients are mixed well and granulated with 10 percent starch paste. The granulation is dried and compressed into tablets using starch as a disintegrant and calcium stearate as a lubricant.

EXAMPLE XIII

Tablets are prepared as described in Example XII except that N-(2,6-dibromophenyl)-N'-(2-imidazolidinylidene)urea is employed as active agent.

EXAMPLE XIV

Gelatin capsules are prepared as described in Example X except that N-(3-chlorophenyl)-N'-(2-imidazolidinylidene)urea is employed as active agent.

What is claimed is:

1. A method which comprises administering to a hypertensive animal, a therapeutically effective antihypertensive amount of a compound selected from the group consisting of (a) an N-aryl-N'-(2-imidazolidinylidene)urea having the formula:

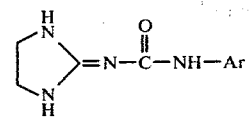

wherein Ar is phenyl substituted with from 0 to 3 substituents independently selected from the group consisting of fluoro, chloro, bromo, methyl, ethyl, methoxy, ethoxy, trifluoromethyl, methylthio, methylsulfonyl, methylsulfinyl and cyano, and (b) a pharmaceutically acceptable salt thereof.

2. A method of reducing arterial pressure in hypertensive subjects which comprises administering to a hypertensive subject from about 5 to 500 milligrams per unit dose of a urea compound represented by the formula

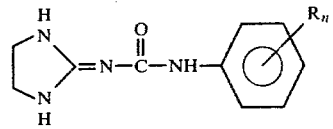

wherein each R is independently selected from the group consisting of chloro, bromo, methyl, ethyl and methoxy, n is an integer of from 0 to 3; and pharmaceutically acceptable salts thereof.

3. A method according to claim 2 in which the urea compound is N-(2,6-dichlorophenyl)-N'-(2-imidazolidinylidene)urea.

4. A method according to claim 2 in which the urea compound is N-(2,6-dimethylphenyl)-N'-(2-imidazolidinylidene)urea.

5. A method according to claim 2 in which the urea compound is N-(2-imidazolidinylidene)-N'-(2-methoxyphenyl)urea.

6. A method according to claim 2 in which the urea compound is N-(2,6-dibromophenyl)-N'-(2-imidazolidinylidene)urea.

7. A pharmaceutical composition in dosage unit form for treating hypertension comprising a therapeutically effective antihypertensive amount of a urea compound selected from the group consisting of (a) an N-aryl-N'-(2-imidazolidinylidene)urea having the formula:

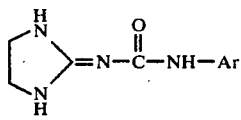

wherein Ar is phenyl substituted with from 0 to 3 substituents independently selected from the group consisting of fluoro, chloro, bromo, methyl, ethyl, methoxy, ethoxy, trifluoromethyl, methylthio, methylsulfonyl, methylsulfinyl, and cyano, and (b) a pharmaceutically acceptable salt thereof; wherein said urea compound is in admixture with a pharmaceutically acceptable carrier.

8. A pharmaceutical composition in dosage unit form comprising per dosage unit from about 5 to 500 milligrams of the active antihypertensive urea compound according to claim 7.

9. A composition according to claim 8 in which the urea compound is N-(2,6-dichlorophenyl)-N'-(2-imidazolinylidene) urea.

10. A composition according to claim 8 in which the urea compound is N-(2,6-dibromophenyl)-N'-(2-imidazolidinylidene)urea.

11. A composition according to claim 8 in which the urea compound is N-(2-imidazolidinylidene)-N'-(2-methoxyphenyl)urea.

12. A composition according to claim 8 in which the urea compound is N-(2-chlorophenyl)-N'-(2-imidazolidinylidene)urea.

13. A method according to claim 2 in which the urea compound is N-(2-chloro-6-methylphenyl)-N'-(2-imidazolidinylidene)urea.

14. A method according to claim 2 in which the urea compound is N-(2-ethyl-6-methylphenyl)-N'-(2-imidazolidinylidene)urea.

15. A composition according to claim 8 in which the urea compound is N-(2,6-dimethylphenyl)-N'-(2-imidazolidinylidene)urea.

16. A composition according to claim 8 in which the urea compound is N-(2-chloro-6-methylphenyl)-N'-(2-imidazolidinylidene)urea.

17. A composition according to claim 8 in which the urea compound is N-(2-ethyl-6-methylphenyl)-N'-(2-imidazolidinylidene)urea.

* * * * *